United States Patent [19]

Pino et al.

[11] 4,186,140

[45] Jan. 29, 1980

[54] PROCESS FOR THE PRODUCTION OF 3-SUBSTITUTED-2,5-DIOXO-TETRAHYDROFURAN

[75] Inventors: Piero Pino, Dolderstrasse 94, Zurich, Switzerland; Denis von Bezard, Vienna, Austria

[73] Assignee: Piero Pino, Zurich, Switzerland

[21] Appl. No.: 879,619

[22] Filed: Feb. 21, 1978

[30] Foreign Application Priority Data

Feb. 21, 1977 [CH] Switzerland ............................ 2115/77

[51] Int. Cl.$^2$ .......................................... C07D 307/60
[52] U.S. Cl. ............................................... 260/346.74
[58] Field of Search ................................... 260/346.74

[56] References Cited

U.S. PATENT DOCUMENTS 3,356,721 12/1967 Wiley ............................... 260/346.74

*Primary Examiner*—Natalie Trousof
*Assistant Examiner*—Bernard Dentz
*Attorney, Agent, or Firm*—Fisher, Christen & Sabol

[57] ABSTRACT

Process for the production of 3-substituted-2,5-dioxo-tetrahydrofuran which involves converting diketene or a substituted diketene in the presence of a catalytic quantity of a carbonyl complex or of a mixture of two carbonyl complexes of metals of the VIIIth group with carbon monoxide and hydrogen at an elevated temperature and an elevated pressure.

17 Claims, No Drawings

PROCESS FOR THE PRODUCTION OF 3-SUBSTITUTED-2,5-DIOXO-TETRAHYDROFURAN

BACKGROUND OF THIS INVENTION

1. Field of This Invention

This invention relates to a process for the production of 3-substituted-2,5-dioxotetrahydrofuran.

2. Prior Art

It is known that compounds having olefinic double bonds, in the case of hydroformylation, react with carbon monoxide and hydrogen in the presence of hydroformylation catalysts, such as, cobalt or rhodium compounds, to produce aldehydes.

BROAD DESCRIPTION OF THIS INVENTION

An object of this invention is to provide a process for the production of 3-substituted-2,5-dioxotetrahydrofuran. Other objects and advantages of this invention are set out herein or are obvious hereform to one ordinarily skilled in the art.

The objects and advantages of this invention are achieved by the process of this invention.

This invention involves the discovery that diketene under hydroformylation conditions does not form aldehydes, as would be expected, but rather methyl succinic acid anhydride (i.e., 3-methyl-2,5-dioxotetrahydrofuran), citraconic anhydride (i.e., 3-methylene-2,5-dioxotetrahydrofuran) and acetone are formed.

The process of this invention for the production of 3-substituted-2,5-dioxotetrahydrofuran is characterized by the fact that diketene or a substituted diketene is converted in the presence of a catalytic quantity of a rhodium complex with carbon monoxide and hydrogen at an elevated temperature and an elevated pressure.

As a useful rhodium complex, above all $Rh_4(CO)_{12}$ is preferably used. This rhodium complex may also be used in connection with the cobalt complex $Co_2(CO)_8$—that is to say, mixtures of such two complexes may be used. The mixture ratio at the same time may be selected advantageously in such a way that the atomic ratio of Rh to Co is between 1:1 and 1:100.

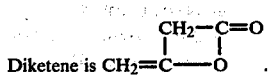

Diketene is 
$$\begin{matrix} CH_2-C=O \\ | \quad\quad | \\ CH_2=C-\!\!-\!\!-O \end{matrix}$$

As a substituted diketene, above all the dimer of methyl ketene is preferably used. Examples of other useful substituted diketenes are the dimer of ethyl ketene, the dimer of dimethyl ketene and the dimer of diphenyl ketene. In general the useful substituted diketenes are the dimers of $R_1CH=C=O$ (i.e., aldoketenes) or $R_1R_2C=C=O$ (ketoketenes), wherein $R_1$ and $R_2$ can be the same or different and are each an alkyl group having 1 to 6 carbon atoms or an aryl group.

The reaction is preferably carried out at a temperature of 50° to 180° C. and most effectively at a temperature of 50° to 150° C.

The total pressure that is used lies effectively between 25 and 400 atm, whereby the $H_2$ partial pressure advantageously amounts to around 5 to 200 atm. The molar ratio between CO and $H_2$ may vary considerably. Advantageously the molar ratio ($CO/H_2$) lies between 20:1 and 0.2:1.

The reaction can be carried out without a solvent or in the presence of a solvent or solvents. As useful solvents, preferably aprotic solvents come into question. Such are, for example, aliphatic or aromatic hydrocarbons, ethers, ketones and anhydrides; specific examples are for example hexane, toluene, diethyl ether, tetrahydrofuran, acetone and acetic acid anhydride.

During the reaction the saturated and unsaturated 3-substituted-2,5,-dioxotetrahydrofurans are mainly formed. As a by-product, ketones are also formed.

In the case of the use of diketene, 3-methyl succinic acid anhydride, citraconic acid anhydride and acetone are formed.

Other useful Group VIII metal carbonyl complexes are the carbonyl complexes of Fe, Ru, Os, Ir, Ni, Pd and Pt.

As a result of the selection of the quantity of the rhodium complex and as a result of the selection of the ratio $CO/H_2$, the quantitative ratios of the developing methyl succinic acid anhydrides and the citraconic acid anhydride can be controlled within certain limits. High temperatures favor the rise in acetone formation.

The most important practical interest lies in the production of the 3-monosubstituted-2,5-dioxotetrahydrofurans. These products may be used as intermediate products in organic chemistry, furthermore as starting products for the production of methyl succinic acid, which itself in turn serves for the production of polymers of softeners (plasticizers). Furthermore, they serve for example, for the production of mono-substituted butylene glycols which serve for the production of condensation polymers as well as for the production of isoprene. The products obtained may also serve as solvents, such as, alkyltetrahydrofurans. The citraconic anhydride may also be used simultaneously.

To repeat, it has been found that diketene under hydroformylation conditions does not form aldehydes as would be expected, but rather methyl succinic acid anhydride (i.e., 3-methyl-2,5-dioxotetrahydrofuran), citraconic acid anhydride (i.e., 3-methylene-2,5-dioxotetrahydrofuran) and acetone are formed.

DETAILED DESCRIPTION OF THIS INVENTION

As used herein, all parts, ratios and percentages are on a weight basis unless otherwise stated herein or otherwise obvious hereform to one ordinarily skilled in the art.

EXAMPLE 1

55.16 gm. of distilled diketene, 50 ccm of benzol and 294 mg. of $Rh_4(CO)_{12}$ were inserted into a dry autoclave, having a capacity of 500 ccm. A dry mixture of CO and $H_2$ (1 to 1) was pressed into the autoclave until reaching a pressure of 100 atm. at room temperature. The autoclave was heated to, and kept at, 90° C. while shaking for 52 hours. Upon reaching the reaction temperature, a drop in pressure was experienced. Additional CO and $H_2$ was continuously forced into the autoclave in such a manner that a constant reaction pressure of 100±5 atm. was maintained.

After the 52 hour period, the autoclave was cooled down and the reaction mixture was analysed with the help of an NMR spectrum. No aldehydes and no unreacted diketene could be found. The reaction product consisted of 14.6 mole percent of methyl succinic acid anhydride and citraconic acid anhydride. The ratio between the two anhydrides was 97 to 3.

EXAMPLE 2

23.2 gm. of diketene, 1036 mg of $Co_2(CO)_8$, 19 mg of $Rh_4(CO)_{12}$ and 50 ccm benzol were inserted into a 500 ccm autoclave. The experiment proceeded as in Example 1, that is to say, CO and $H_2$ were used in a ratio of 1:1, a temperature of 83° C. was used and the reaction pressure was maintained for 32 hours at 130±5 atm. 13 gm. of methyl succinic acid anhydride (3-methyl-2,5-dioxotetrahydrofuran) was obtained by distillation. The yield amounted to 44 percent of theoretical.

EXAMPLE 3

As in Example 2, 11 gm. of diketene, 547.1 mg of $Co_2(CO)_8$, 54.3 mg of $Rh_4(CO)_{12}$ and 10 ccm of benzol were caused to react at 100° C. and a constant pressure of 110 atm with a CO and $H_2$ mixture for 5 hours. In the case of a conversion of 58 percent of the diketene, methyl succinic acid anhydride (related to the converted diketene) was obtained at a yield of 62 percent.

EXAMPLE 4

42.6 gm. of diketene, 1954 mg of $Co_2(CO)_8$, 97 mg of $Rh_4(CO)_{12}$ and 50 ccm of benzol were converted in a 500 ccm autoclave during 8 hours at 84° C. and a constant pressure of 300 atm with a mixture of CO and $H_2$ in a ratio of 2 to 1. The reaction products were first distilled at standard pressure—subsequently an additional distillation took place at a pressure of 0.1 mmHg. 12.3 gm. of acetone (yield 36.7 percent) was obtained as a low boiling portion. The high boiling portion consisted of 35.7 gm. of practically pure 3-methyl-2,5-dioxotetrahydrofuran which corresponds to a yield of 54 percent.

EXAMPLE 5

5.2 gm. of diketene, 100 mg of $Co_2(CO)_8$, 10 mg of $Rh_4(CO)_{12}$ and 3.4 gm. of benzol were converted in a 150 ccm autoclave at 80° C. and a constant pressure of 20 atm with a mixture of CO and $H_2$ in a ratio of 9 to 1. The autoclave was cooled down after 6 hours. The reaction products, after gas chromatographic analysis, contained 3.9 gm. of unconverted diketene and 0.07 gm. of acetone (8 percent of theoretical with reference to the converted diketene). After an NMR analysis, the reaction products contained 1.4 gm. of 3-methyl-2,5-dioxotetrahydrofuran (yield calculated with reference to the converted diketene was 80 percent).

What is claimed is:

1. Process for the production of 3-substituted-2,5-dioxotetrahydrofuran characterized in that diketene or a substituted diketene is converted in the presence of a catalytic quantity of a carbonyl complex of a metal or carbonyl complexes of metals of the VIIIth group with carbon monoxide and hydrogen at an elevated temperature and an elevated pressure.

2. Process as claimed in claim 1 wherein $Rh_4(CO)_{12}$ is the carbonyl complex of a metal of the VIIIth group.

3. Process as claimed in claim 1 wherein a catalytic quantity of mixtures of carbonyl complexes of metals of the VIIIth group is used.

4. Process as claimed in claim 3 wherein a mixture of $Rh_4(CO)_{12}$ and $Co_2(CO)_8$ is used as the carbonyl complexes of metals of the VIIIth group.

5. Process as claimed in claim 4 wherein the mixture of $Rh_4(CO)_{12}$ and $Co_2(CO)_8$ is used with the ratio of Rh to Co being between 1:1 and 1:100.

6. Process as claimed in claim 3 wherein metals of the VIIIth group, which form carbonyl complexes under the reaction conditions, are used as catalyst.

7. Process as claimed in claim 3 wherein compounds of metals of the VIIIth group, which form carbonyl complexes under the reaction conditions, are used as catalysts.

8. Process as claimed in claim 1 wherein the conversion is carried out at a temperature between 50° and 180° C.

9. Process as claimed in claim 1 wherein a metal of the VIIIth group, which forms the corresponding carbonyl complex under the reaction conditions, is used as catalyst.

10. Process as claimed in claim 1 wherein metal compounds of the VIIIth group, which form carbonyl complexes under the reaction conditions, are used as catalysts.

11. Process as claimed in claim 1 wherein the reaction is carried out at a pressure between 25 and 400 atm.

12. Process as claimed in claim 1 wherein the carbon monoxide and hydrogen are used in a molar ratio of 100:1 to 0.2:1.

13. Process as claimed in claim 1 wherein the conversion is carried out in the presence of an aprotic solvent.

14. Process as claimed in claim 1 wherein diketene is converted.

15. Process as claimed in claim 1 wherein $Rh_4(CO)_{12}$ is the carbonyl complex of a metal of the VIIIth group, the conversion is carried out at a temperature between 50° and 180° C., the conversion is carried out at a pressure between 25 and 400 atm., and the carbon monoxide and hydrogen is used in a molar ratio of 100:1 to 0.2:1.

16. Process as claimed in claim 13 wherein diketene is converted.

17. Process as claimed in claim 13 wherein a substituted diketene is converted.

* * * * *